United States Patent
Toffoli et al.

(10) Patent No.: US 10,788,470 B2
(45) Date of Patent: Sep. 29, 2020

(54) COMPACT GAS SENSOR WITH ENHANCED SELECTIVITY

(71) Applicant: COMMISSARIAT A L'ENERGIE ATOMIQUE ET AUX ENERGIES ALTERNATIVES, Paris (FR)

(72) Inventors: Valeria Toffoli, Grenoble (FR); Thomas Alava, Grenoble (FR); Bertrand Bourlon, Saint Martin le Vinoux (FR); Eric Ollier, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 339 days.

(21) Appl. No.: 15/388,673

(22) Filed: Dec. 22, 2016

(65) Prior Publication Data
US 2017/0184556 A1 Jun. 29, 2017

(30) Foreign Application Priority Data
Dec. 23, 2015 (FR) ...................................... 15 63217

(51) Int. Cl.
*G01N 30/00* (2006.01)
*G01N 30/95* (2006.01)
(Continued)

(52) U.S. Cl.
CPC ............... *G01N 30/95* (2013.01); *G01N 5/04* (2013.01); *G01N 25/4833* (2013.01);
(Continued)

(58) Field of Classification Search
None
See application file for complete search history.

(56) References Cited

U.S. PATENT DOCUMENTS 7,299,711 B1 * 11/2007 Linker ................. G01N 1/2214
73/863.23
7,694,346 B2 * 4/2010 Adams ................. G01N 29/036
850/7
(Continued)

FOREIGN PATENT DOCUMENTS

WO WO 01/40793 A1 6/2001

OTHER PUBLICATIONS

Search Report dated May 18, 2017 in European Patent Application No. 16206507.2 (with English translation of categories of cited documents).
(Continued)

*Primary Examiner* — Paul S Hyun
(74) *Attorney, Agent, or Firm* — Oblon, McClelland, Maier & Neustadt, L.L.P.

(57) ABSTRACT

A microelectromechanical gas sensor including a fixed part, at least one suspended part in relation to fixed part, at least one sensitive zone carried on the suspended part, the sensitive zone being able to adsorb/absorb and desorb gaseous species or families of gaseous species, a heater for heating at least the sensitive zone, a detector for detecting the adsorption/absorption and desorption of gaseous species or families of gaseous species on the sensitive zone, a controller of controlling the heater so that the heating is applied to at least the sensitive zone with one or more temperature profiles ensuring the adsorption/absorption and desorption of the gaseous species in a controlled manner so as to obtain an individual desorption of each species or families of gaseous species.

23 Claims, 8 Drawing Sheets

(51) Int. Cl.
*G01N 25/48* (2006.01)
*G01N 5/04* (2006.01)
*G01N 33/00* (2006.01)

(52) U.S. Cl.
CPC ..... *G01N 33/0016* (2013.01); *G01N 33/0029* (2013.01); *G01N 33/0031* (2013.01); *G01N 33/0059* (2013.01)

(56) References Cited

U.S. PATENT DOCUMENTS

| | | |
|---|---|---|
| 2005/0090018 A1 | 4/2005 | Walte et al. |
| 2008/0085212 A1 | 4/2008 | Adams et al. |
| 2010/0055801 A1 | 3/2010 | Yi et al. |
| 2015/0107336 A1 | 4/2015 | Hentz et al. |

OTHER PUBLICATIONS

Matthew Kasper, "Simultaneous Nanothermal Analysis Using Heated Microcantilevers", University of Illinois at Urbana-Champaign, XP055371249, 2010, 31 pages.

Valeria Toffoli et al., "Heater-Integrated Cantilevers for Nano-Samples Thermogravimetric Analysis", Sensors, vol. 13, No. 12, XP055371168, Dec. 2013, pp. 16657-16671.

Rudiger Berger et al., "Thermal Analysis of Nanogram Quantities Using a Micromechanical Cantilever Sensor", Manuscript for 30$^{th}$ Conference on Thermal Analysis and Applications, NATAS 2002 Conference Pittsburgh, XP055371183, 2002, 6 pages.

Elina Iervolino et al., "MEMS for Thermogravimetry; Fully Integrated Device for Inspection of Nanomasses", Journal of Microelectromechanical System, vol. 20, No. 6, XP011379423, 2011, pp. 1277-1286.

U.S. Appl. No. 14/009,959, filed Feb. 14, 2014, US 2014-0166085 A1, Emmanuel Ollier.

U.S. Appl. No. 14/128,266, filed Feb. 25, 2014, US 2014-0158334 A1, Olivier Dellea et al.

U.S. Appl. No. 14/514,703, filed Oct. 15, 2014, US 2015-0329986 A1, Eric Ollier et al.

U.S. Appl. No. 14/430,762, filed Mar. 24, 2015, US 2015-0243871 A1, Emmanuel Ollier.

U.S. Appl. No. 15/000,473, filed Jan. 19, 2016, US 2016-0225975 A1, Emmanuel Ollier.

U.S. Appl. No. 15/000,744, filed Jan. 19, 2016, US 2016-0211436 A1, Emmanuel Ollier et al.

U.S. Appl. No. 15/000,904, filed Jul. 21, 2016, US 2016-0209080 A1, Emmanuel Ollier et al.

U.S. Appl. No. 15/209,067, filed Jul. 13, 2016, US 2017-0016840 A1, Bertrand Bourlon et al.

U.S. Appl. No. 15/283,827, filed Oct. 3, 2016, US 2017-0103936 A1, Ulrich Soupremanien et al.

U.S. Appl. No. 15/378,448, filed Dec. 14, 2016, Ulrich Soupremanien et al.

Search Report dated Aug. 3, 2016 in French patent application No. 1563217 (with English translation of categories of cited documents).

Kunal Pharas et al., "Knudsen pump driven by a thermoelectric material", Journal of Micromechanics and Microengineering. vol. 20, No. 12, Nov. 29, 2010, 1 page (submitting English abstract only).

\* cited by examiner

COMPACT GAS SENSOR WITH ENHANCED SELECTIVITY

FIELD OF INVENTION AND PRIOR ART

The present invention relates to a gas sensor providing enhanced selectivity, in compact form and an analysis process implementing said gas sensor.

More and more, gas composition analyses of the environment are carried out, for example, to detect pollution. On average, humans pass more than 80% of their existence indoors, thus the quality of indoor air is monitored and controlled, particularly due to the use of new synthetic chemical materials used in building construction.

Numerous sensors are able to carry out quantitative detection of gases in trace forms. There are sensors that detect a modification in the physical properties of the external environment, as is the case with thermal conductivity sensors that are sensitive to modifications of the outdoor thermal conductivity coefficient. There are also sensors that are sensitive to the absorption of gaseous species on a surface, this type of sensor has a sensitive surface that favours adsorption and/or desorption.

However, there do not exist sensors that are sensitive to a single gaseous species. The result of this is that to discriminate between gas species contained in a mixture, the sensor is associated with an arrangement capable of separating in time and/or space the gaseous species in order to correlate the contribution of the various species to the sensor's response.

For example, filters or chromatography columns are used, associated or otherwise with pre-concentrators to ensure such separation. A chromatography column ensures the separation of each of the species but has the disadvantage that it is difficult to integrate into a compact analysis device. Furthermore, it requires a certain quantity of thermal energy for its operation as well as the supply of a carrier gas. There are gaseous phase micro-columns that can be integrated into silicon microchips, but they still require an important degree of heating and a carrier gas source.

Concerning the pre-concentration devices, these permit the detection of traces but generally require a large volume, particularly to maximise the number of species collected. The also require heating with good dynamics to ensure the rapid liberation of the pre-concentrated species, particularly when they are coupled with a chromatography column.

These separation devices are therefore cumbersome and consume a great deal of energy.

Document WO01/40793 describes a device comprising a material able to adsorb and desorb gases, a heating means for this material and a selective gas sensor. The species adsorbed by the material are desorbed on heating and are then detected by the selective gas sensor. This arrangement is bulky.

Document US 2005/0090018 describes a device for detection of volatile organic compounds (VOCs) in high concentrations, comprising an adsorbent membrane and a gas sensor. A means of heating applies a thermal shock to the membrane, desorbed species cross the membrane and are detected by the sensor. This arrangement is likewise bulky.

Furthermore, present research seeks to integrate gas sensors into portable electronic devices such as mobile phones or personal digital assistants, for example to detect safe environments, or those containing pollutants.

OBJECTS AND ADVANTAGES OF THE INVENTION

Consequently, one aim of the present invention is to provide a highly compact gas sensor while providing enhanced selectivity.

The above stated aim is attained with a sensor having one part suspended in relation to a fixed part, at least one sensitive zone on the suspended part, said sensitive part being able to adsorb/absorb and desorb at least two gaseous species, with detection means for detecting the adsorption and desorption of at least two gaseous species, heating means for heating said sensitive zone and control means for controlling the heating, in such a way as to apply one or more temperature profiles to the sensitive zone in order to generate at least one phase of adsorption and one phase of desorption.

By 'temperature profile' is meant a change in the temperature applied to the sensitive zone as a function of time. This profile may, for example, comprise a phase of constant temperature maintaining for a given period and provoking the adsorption and another constant temperature maintaining a higher temperature provoking the desorption, or phases of temperature variation the temperature varying by steps or according to a square signal or in a monotone manner or otherwise, it may also include a sinusoidal variation at constant or variable frequency or pulses.

By selecting the temperature profile or profiles, it is possible to increase the selectivity of the sensor in relation to certain gaseous species, for example by adsorbing/absorbing all the gaseous species then by desorbing one by one the gaseous species. The successive adsorption then desorption can be detected for example by measuring a variation in the electrical resistance of the sensitive zone or by detection of a variation in the resonance frequency of the suspended part.

In other words, we employ the sensitive zone or zones of the sensor which is/are temperature controlled, as a separation device for the gaseous species. And we carry out real-time control of the stationary and/or dynamic interactions of the species contained in the gas and the sensitive zone or zones to ensure their separation.

The sensor according to the present invention provides greater selectivity and is highly compact since it integrates the means of separation, contrary to certain sensors that need to be associated with a gas chromatography column that first separates the gaseous species that are only then detected by the sensor.

The sensor according to the invention thus integrates the functions of collection, separation and detection for the gaseous species. It therefore offers increased identification capacity.

Advantageously, the sensor according to the invention can be integrated into a detection system and be associated with other MEMS and/or NEMS types sensors to enhance the selectivity of the detection system, for example, by correlating the signals emitted by the different sensors.

In one highly advantageous embodiment, the sensors of the detection system can interact between themselves by exchanging the gaseous analytes. They can collect, detect and separate the species of the gaseous mixture in a specific and complementary manner. Certain analytes may be detected by several sensors sequentially. In a variant, the sensors can be used in the same manner forming, for example, a network of several sensors targeting different gaseous species.

The subject-matter of the present invention is therefore a microelectromechanical and/or nanoelectromechanical gas sensor comprising:
- a fixed part,
- at least one part suspended in relation to the fixed part,
- at least one sensitive zone carried on the suspended part, said sensitive zone being able to adsorb/absorb and desorb the gaseous species or families of gaseous species,
- a heating means for at least the sensitive zone,
- a detection means for the adsorption/absorption and desorption of gaseous species or families of gaseous species on the sensitive zone,
- a control means of the heating means so that the heating means can apply at least to the sensitive zone one or more temperature profiles, ensuring the adsorption/absorption and desorption of the gaseous species in a controlled manner, so as to obtain an individual desorption of each species or families of gaseous species.

Another subject-matter of the present invention also is a microelectromechanical and/or nanoelectromechanical gas detection system comprising at least one first gas sensor according to the invention and at least one second gas sensor and a comparison and processing means for the signals issuing from the detection means of each of said sensors.

Another subject-matter of the present invention is a gaseous mixture analysis method implementing a sensor according to the invention or a detection system according to the invention, and comprising at least one cycle of the following steps:

a) application to at least one sensitive zone in a reference state at least one temperature to provoke an adsorption/absorption of gaseous species, b) measurement of a detection signal of the adsorption/absorption, c) application of at least a second temperature to provoke the desorption of at least part of the gaseous species, d) measurement of a detection signal from said desorption, e) repetition of the cycle until all the species of interest are separated.

DESCRIPTION OF DRAWINGS

The present invention is better understood on the basis of the description that follows and the appended drawings, in which.

DESCRIPTION OF INVENTION

Figure 1:
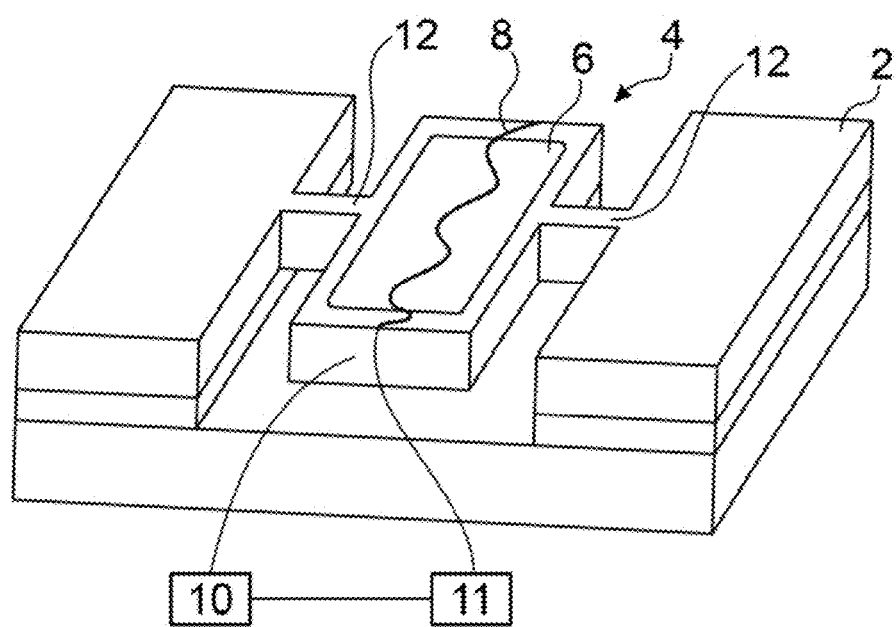
FIG. 1 is a schematic representation of one embodiment of the sensor according to the invention.

FIG. 1 is a schematic representation of an embodiment of the gas sensor according to the invention.

According to the invention the gas sensor is a microelectromechanical and/or nanoelectromechanical gas sensor. It will designated microelectronic gas sensor.

The gas sensor is intended to detect gaseous species contained in a gaseous mixture. These species are potentially present in the gaseous mixture, the presence of each and their concentration is sought to be detected. For example, seeking to detect the appearance of a dangerous species, for example a pollutant, the species having being previously identified. The sensor is therefore suited to the detection of certain species, particularly at the level of the sensitive zone and temperature control means of the sensitive zone. In a preferred embodiment, the sensor is a microelectromechanical system (MEMS) and/or Nanoelectromechanical system (NEMS).

The sensor comprises a fixed part 2, a suspended part 4 suspended in relation to fixed part 2, a sensitive zone 6 carried by the suspended part 4, heating means 8 for heating the at least sensitive zone 6.

Sensitive zone 6 is able to adsorb/absorb and desorb the gaseous species, also known as analytes. In the following description, the term «adsorption» shall be used to designate both adsorption and absorption.

The sensor also comprises means 10 to detect physicochemical changes within the sensitive zone provoked by the adsorption and desorption of gaseous species on the sensitive zone. The detection means 10 shall be described later.

The use of a suspended part permits limiting thermal losses and focussing the heating, the energy required for heating the sensitive zone is thus advantageously reduced.

The suspended part is for example in the form of a membrane or in the form of a bridge suspended in relation to the fixed part, for example by means of beams 12 of thin section in order to advantageously limit even further the thermal losses of suspended part 4 to the fixed part and to focus the heating. The membrane can be supported by one or several pillars.

The suspended part can be in the form of a disk suspended by the beams. In a variant, the suspended part is of a nano-wire type or embedded beam, preferably with the form and cross-section of the beam optimised to improve detection sensitivity. In one advantageous embodiment, in the case of a suspended part formed by a suspended beam, the beam would have a cross-section of 160 nm by 200 nm.

The sensitive zone 6 comprises a layer formed on at least one of the faces of the suspended part, the layer covering all or part of one or two faces of the suspended part. Preferentially, the layer has a substantially constant thickness. The choice of material of the layer forming the sensitive zone is selected in relation to the species that are sought to be detected in the mixture to analyse.

The sensitive layer comprises at least one material able to adsorb the species of interest. The sensitive layer may comprise a single material or be enriched. The selection of the sensitive layer depends on the species of interest to analyse, for example whether an organic or inorganic species . . . .

For example, it may be a porous polymer resin, such as Tenax TA®, Tenax GR®, Carbotrap®, Carboxen®, or Carbosieve® used to detect volatile or semi-volatile organic compounds and discriminate the compounds.

According to other embodiments, it may be:
- a mesoporous silica powder with the channels oriented in two directions, such as SBA (Santa Barbara Amorphous) and MCM (Mobile Crystalline Materials), or in porous silicon,
- alumina ($Al_2O_3$) with pores of different dimensions or with pores functionalized by chemical radicals providing different physico-chemical properties, particularly suited for the adsorption of VOCs,
- porous material forming the suspended part of the MEMS and/or NEMS, for example porous silicon,
- carbon nanotubes, both single-walled carbon nanotubes (SWNTs) and multi-walled carbon nanotubes (MWNTs) that are efficient in adsorbing a wide variety of pollutants. (please provide an example of a pollutant).

The sensor also comprises control means of the heating means in such a way as to apply temperature profiles to the sensitive zone in relation to the gaseous mixture to analyse.

The heating means may be of the Joule effect type, the electrical current circulating in the suspended part being of a material such that the passage of current generates heat, for example, a electrical conductor on the suspended part provoking heating of the sensitive zone. In one variant, it may be a heating means by thermal radiation, this for example arranged on the fixed part facing the suspended part. Other heating techniques can be employed, for example electrical structures using Peltier and Seebeck effects.

Advantageously, a thermal diffusion layer may be used on the suspended part to ensure a homogenous temperature of the sensitive zone.

In a highly advantageous manner, the sensor comprises temperature measurement means at the level of the sensitive zone in order to better control the heating means and control the different steps of the analysis. For example, these measurement means comprise a thermocouple arranged on the suspended part so as to measure the temperature of the sensitive zone. By measuring the resistance of the conducting wire forming the thermocouple the temperature of the sensitive zone is learnt. As variants, the means of measurement may be of the contactless type, for example infrared or laser means of determining the temperature.

The detection means may be of several types.

In one embodiment, the suspended part is mobile.

The detection means can be of the resonating micro gravimetric type. For this the suspended part is placed in movement through the action of an excitation means at its resonance frequency. When one or more gaseous species are adsorbed or desorbed on the sensitive zone, the resonance frequency varies. By measuring this variation, we can detect the species adsorbed or desorbed and their quantity.

The excitation or movement means for the suspended part can be for example, of the electrostatic, magnetic, piezoelectric, opto-mechanical or thermal type.

The movement measurement means are for example, of the electrical, electrostatic, piezo resistive, piezoelectric or magnetic type.

In another embodiment, in which the suspended part is fixed, the detection means can be of the resistive type, i.e. the sensitive zone is for example in a conductor or semiconductor material, the adsorption and desorption of gaseous species provoking a modification of the electrical conductivity of the sensitive zone that can be detected by suitable electrical detection means.

Heating means of the Joule effect type can be used as detection means of the resistive type.

The sensor according to the invention may function either in a stationary regime, or a transitory or dynamic regime.

In a stationary state, i.e. independent of time, the concentration of analyte on the sensitive zone can be expressed in terms of the fraction of active sites occupied by molecular species (1−θ). For an adsorption on a single layer, the variation of the fraction as a function of time is expressed:

$$\frac{d\theta}{dt} = k_{ads}(1-\theta)c - k_{des}\theta \qquad 1)$$

Where c is the concentration of analyte in the gas, $k_{ads}$ the advancement constant of the adsorption reaction and $k_{des}$ the advancement constant of the desorption reaction.

By supposing a homogenous surface and that the atoms of adjacent sites do not interact, we can express a stationary state:

$$k_{ads}(1-\theta_e)c - k_{des}\theta_e = 0 \qquad 2)$$

$$\theta_e = \frac{1}{1+ck_{eq}}$$

$$k_{eq} = \frac{k_{ads}}{k_{des}} = \frac{\theta_e}{(1-\theta_e)c}$$

$K_{eq}$ being the equilibrium constant.

In the case of multi-layer adsorption, and by supposing a system of limited reactions, the equilibrium constant $k_{eq}$ can be written:

$$k_{eq} = \frac{c_s}{c} = \frac{1}{c}\frac{\Delta m}{MSt} \approx \frac{1}{c}\frac{\Delta m}{MS} \qquad (3)$$

Where $c_s$ is the concentration of gas at the sensitive zone in mol/m³, c is the concentration of the analyte in the gaseous mixture in mol/m³, M is the molar mass (g/mol), S is the surface area of the sensitive zone in m² and t (m) the thickness of the sensitive zone.

Knowledge of $K_{eq}$ allows discrimination of the different gaseous species, for example a high equilibrium constant $k_{eq}$ is characteristic of high affinity between the gaseous species and the active layer.

It is therefore possible to distinguish different species.

Similarly, in a transitory or dynamic state, i.e. in which time is taken into account in the variation of the quantity of species adsorbed and desorbed, the kinetic evolution of the adsorptions and desorptions depends on the concentration in gaseous species, the kinetic parameters and the density of the adsorption sites available. The response over time of the sensitive zone supplies constants, that can be used to discriminate gaseous species in terms of affinities between species and the layer of the sensitive zone, the kinetic evolution is expressed in times of adsorption $\tau_{ads}$ and the time necessary for the layer of the sensitive zone to become functional again $\tau_{des}$:

It can be written:

$$\tau_{ads} \propto \frac{1}{k_{ads}c + k_{des}} \quad \text{4)}$$

and $$\tau_{des} \propto \frac{1}{k_{des}}$$

Moreover, the reaction speed depends on the speed according to the Arrhenius equation:

$$r = -\frac{\partial \sigma}{\partial t} = k_0 \sigma^n e^{-\frac{t}{\tau}} \quad \text{(5)}$$

$$k_{eq} = \frac{k_{ads}}{k_{des}} = \alpha * \exp\left[\frac{E_{des} - E_{ads}}{RT} t\right]$$

Where r is the speed of reaction in mol/cm³ sec, E the activation energy in kJ/mol, σ" the percentage of the surface that interacts with the gas, n the order of the process and $k_0$ the pre-exponential factor, this latter parameter takes into account the speed of variation of the temperature, the initial adsorbed concentration and the activation energy.

From this it results that the constants $\tau_{ads}$ and $\tau_{des}$, $k_{eq}$ can be used as a discrimination factor.

Thus each gaseous species having a different affinity with the layer of the sensitive zone, a different adsorption speed and different desorption speed, it is possible by applying temperature profiles to the sensitive zone to separate the gaseous species. The control means are then programmed to apply suitable temperature profiles to analyse given species. The detection means by measuring a variation, for example in the resonance frequency of the suspended part, or its conductivity, permits the determination of which species or families of species are present in the gaseous mixture and in what quantity.

We shall now describe examples of the temperature profiles that can be applied to the sensitive zone by the heating means in relation to commands issued by the control means.

Firstly, the profiles suited to the stationary regime will be described.

Figure 2A:
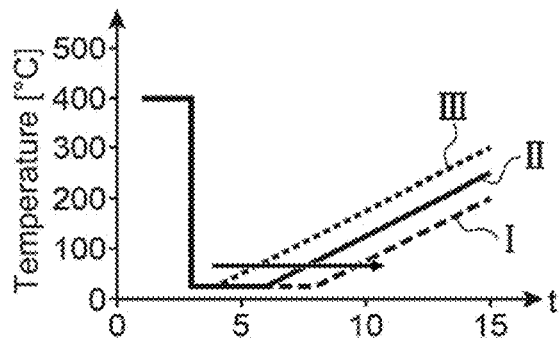
FIGS. 2A to 2F are graphic representations of examples of temperature profiles able to be applied to the sensitive zone of the sensor.
Figure 2B:
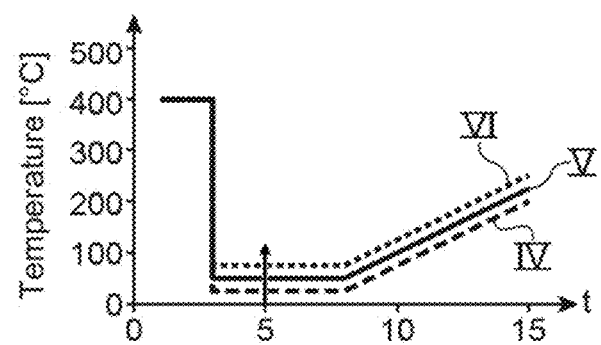
Figure 2C:
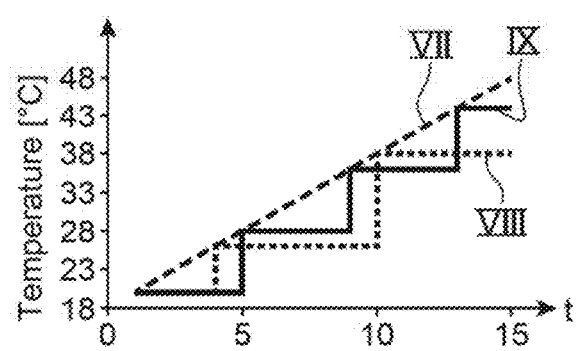

The profiles in FIGS. 2A to 2C are profiles suited to adsorption.

In FIG. 2A, we see different temperature profiles as a function of time suited to an adsorption step. Shown are three different profiles I, II, III that present a constant temperature zone for a given period, this duration increasing from profile I to profile III. By varying the duration of a constant temperature phase, the quantity of species adsorbed is increased.

In FIG. 28, are three temperature profiles IV, V, VI at constant temperature, the temperatures being different, and the durations equal, the temperature increases from profile IV to profile VI.

FIG. 2C shows profile VII imposing a linearly increasing temperature over time and the two profiles VIII and IX imposing an increase in temperature per step. All species do not necessarily adsorb at the same temperature, we can by imposing an increase in the adsorption temperature detect the adsorption of different species as the temperature increases.

The monitoring of the adsorption is carried out by the detection means which detect the variation of the quantity of species adsorbed. During adsorption, all or part of the species is adsorbed simultaneously.

Figure 2D:
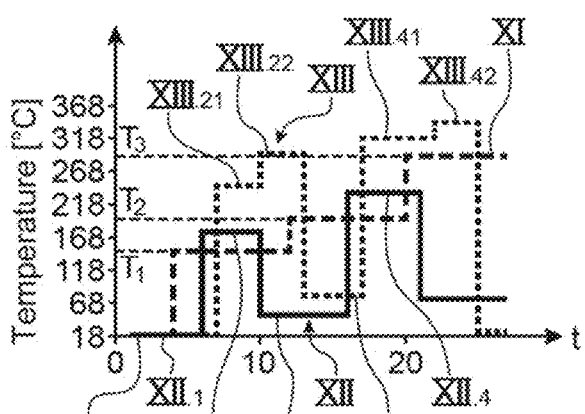

In FIG. 2D, we see profile XI adapted to the desorption and which comprises increasing temperature steps. At each step a species or family of species is desorbed. Each desorption of a species or family of species provokes a variation in the physical quantity of detection, this variation is measured by the detection means. This variation is both relative to the species of family of species desorbed and the quantity desorbed. The temperature values of the steps are selected so as to each desorb a species or family of species adsorbed. For example, if the gaseous mixture comprises three species A, B, C that are adsorbed by the sensitive zone and that A desorbs at temperature T1, that B desorbs at temperature T2 and C desorbs at temperature T3 greater than T2. By applying the desorption profile XI, the species A, B, C will be desorbed separately and the detection means will detect each desorption.

Profile XII is such that it permits the alternation of the adsorption and desorption phases. For example, the portions XII.1, XII, 3 are isotherms permitting adsorption and portions XII.2 and XII.4 are isotherms permitting desorption.

By alternating the phases of adsorption and desorption we can refine the knowledge of the species adsorbed. For example, adsorption XII.1 can be carried out 'blind' and desorption XII.2 also so. Then having detected a desorption, the temperature of adsorption XII.3 is increased in order to target even more the species. Then, in the example shown, the desorption temperature XII.4 is also increased. We can envisage adapting the profile in relation to the measurements carried out by the detection means in order to better target the species or to apply already programmed profiles. In fact, if nothing is adsorbed by increasing the adsorption temperature, that signifies that this temperature is at least equal to that of desorption. The adsorption and desorption are therefore to be modified.

Profile XIII is adapted to the analysis of a gaseous mixture comprising at least two species or two families of species. The profile comprises phases desorption with two steps, thus permitting two successive desorptions at two different temperatures.

If we consider a gaseous mixture comprising three species A, B, C.

During phase XIII.1 the three species are adsorbed.

During phase XIII.21, the species B and C are desorbed and during phase XIII.22 species A is desorbed.

During phase XIII.3, a new phase of adsorption takes place, only species B and C are adsorbed.

During phase XIII.41 species B is desorbed and during phase XIII.42 species C is desorbed.

Thus the three species were able to be separated and the variation in the physical parameter relating to the desorption of each species was able to be measured. We can then identify each species and the quantity adsorbed. We can then trace the concentration of each species in the gaseous mixture.

In a dynamic regime, the times or speeds of absorption and desorption can be used to detect the different species.

Figure 2E:
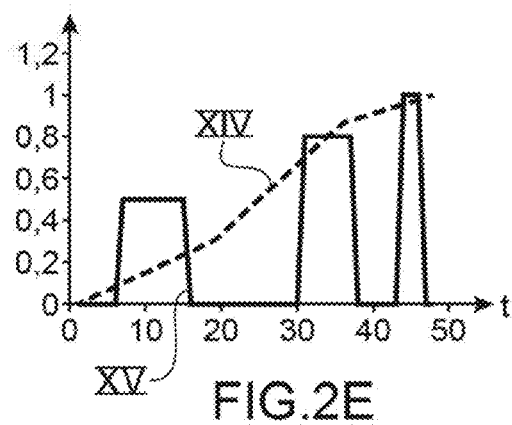

In FIG. 2E, we see two examples of temperature profiles suited to a dynamic regime analysis and in which we observe both the adsorption and the desorption. Profile XIV comprises a series of increasing ramps and profile XV comprises pulses whose extremum increases with each pulse, the pulses may have or not have identical or different durations.

Figure 2F:
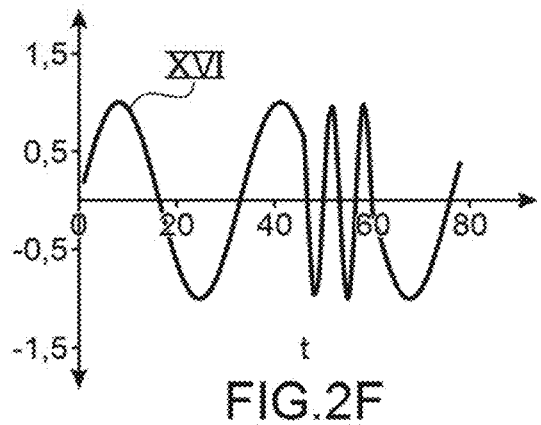

In FIG. 2F, profile XVI is a sinusoidal signal, the amplitude of the signal in constant over time but the frequency is variable. Inversely, one can foresee a signal of variable amplitude and constant frequency. For example, a signal controlling the heating means and having several frequencies can directly modify the reaction kinetics on the sensitive zone.

In FIGS. 2E and 2F the temperature on the y-axis is normalized.

The signal in a dynamic or transitory regime can combine sinusoidal signals, ramps of pulses at different frequency, noise. In fact, the noise of a frequency response can allow discrimination of the gaseous species in an environment.

The functioning of the sensor in dynamic regime can allow better detection of desorption which can be very rapid. In fact, by continuously increasing the temperature we continuously pass from a phase of adsorption to a phase or phases of successive desorption. In the case of a detection mode in a stationary regime, for example by applying step profiles, the time required to reach the step level, the desorption for at least one species may already be completed. Thus the functioning of the sensor in dynamic regime can allow detection of the desorptions of specific species and to thus identify them in relation to the desorption of other species if the desorption of the species being sought has a too rapid dynamic or an associated temperature too close to the desorption temperature of the gaseous species present in the mixture but not being sought. The use of a static or dynamic functioning is selected in relation to the gaseous mixtures, the gaseous species being sought and the appropriateness of the sought species to the physico-chemical characteristics of the sensitive layers retained. The two modes of operation can be used to increase the selectivity of the sensor, either separately or at the same time.

When the operating mode of the sensor involves adsorbing and desorbing several times either all or part of the gaseous species on the same sensitive zone of the same sensor, as for example is the case in profiles XII, XIII, XVI, the volume of the gas is isolated from the external environment in the neighbourhood of the sensor. The sensor can then be integrated into fluidic or micro-fluidic channel that is connected to a gaseous circulation system and a system of channel input and output valves. The closing of the valves allows confining the gas mixture to be analysed in the neighbourhood of the sensor for a controlled time during the analysis. Very advantageously, the valves are of the normally closed type, they are thus actuated to permit a gas mixture to be analysed to enter the channel, this permits reducing electrical consumption.

In the case where several sensors having the same sensitive layer are used, as will be described below, we also foresee maintaining the volume of gas isolated from the external environment in the neighbourhood of the sensors.

When implementing several sensors we can foresee sequentially adsorbing or desorbing several times the gaseous species on the sensitive layers of the sensors, the confinement of the sensors can be carried out by integrating them in the structure of a fluidic or microfluidic channel produced by assembling two structured plates using classical micro-fabrication techniques. The channel may be advantageously connected to a gas circulation system, for example a pump which imposes a directional flow on the gas, which permits desorbing and adsorbing species on the different sensitive zones of the different sensors according to a given spatial order. In the absence of a gas circulation system, the species move from one sensor to another in both directions of the microfluidic channel and solely by diffusion.

We shall now give an example of measurement in a stationary regime carried out on a gas mixture comprising at least three species A, B and C.

Figure 10:
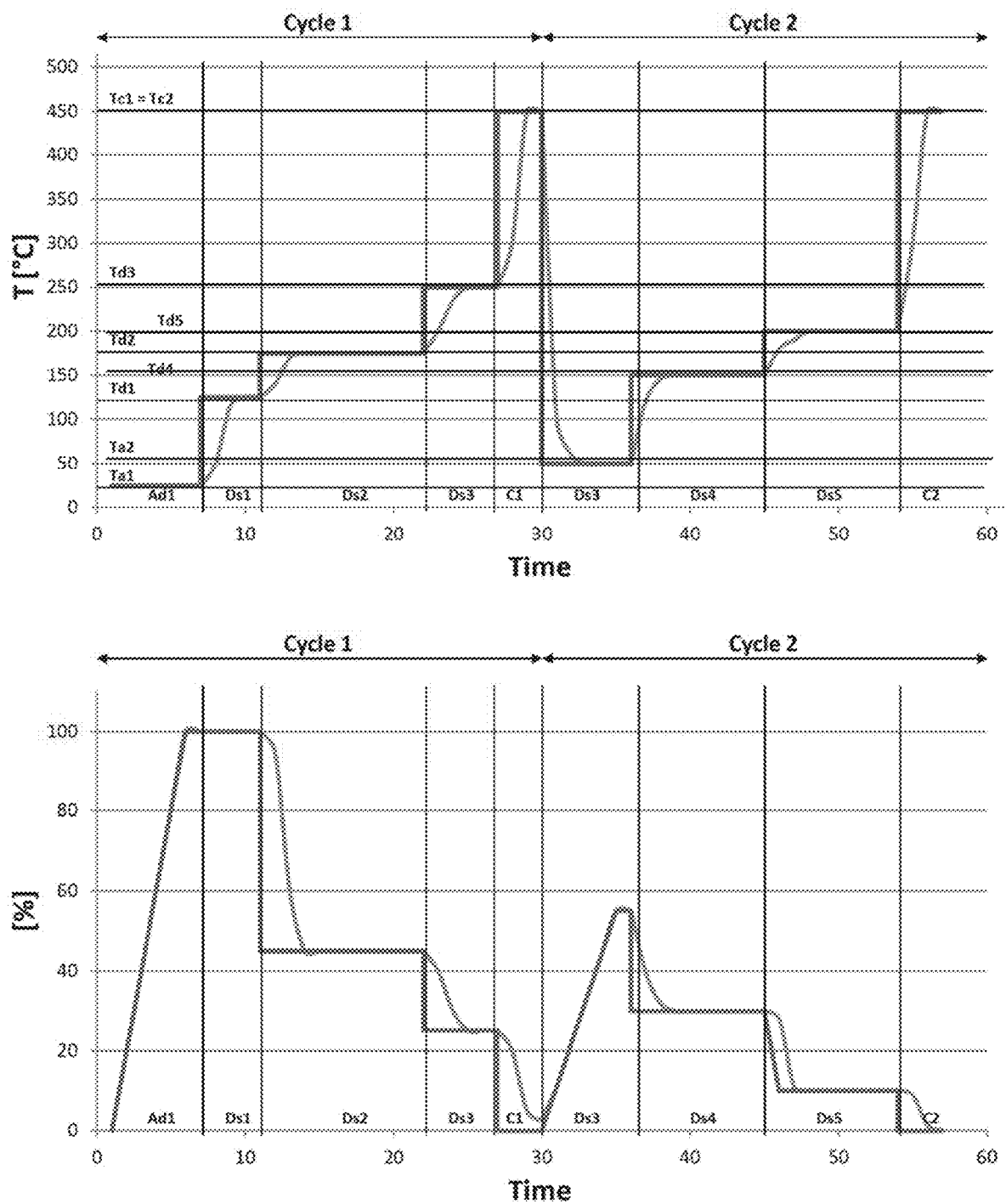
FIG. 10 is a graphic representation of an example of a temperature profile applied to a sensor according to the invention and the signal emitted by the detection means as a function of time.

The temperature profile and the signal from the detection means as a function of time t are shown in FIG. 10.

The temperature profile comprises two cycles, each cycle having an adsorption phase for species A, B and C and successive desorption phases.

The dark line indicates the instruction or ideal response and the clear line indicates the real response.

The adsorption phases are designated Ad1 and Ad2 and the desorption phases are designated Ds1 to Ds6.

The detection means supply signals during each phase, these are designated Sa1 and Sa2 for the phases Ad1 and Ad2 and Ds1 to Ds6.

The signals are expressed as percentages, the signal during the first phase of adsorption equals 100%, when at least a part of the species is desorbed the signal is less than 100%.

The heating means are commanded by the control means to apply during phase Ad1 a temperature Ta1. The signal Sa1 is largely composed of a linear function characteristic of a continuous variation of the quantity of species adsorbed. In the example shown, the value of the physical characteristic increases but it is understood that it could also diminish.

During phase Ds1 a temperature Td1 greater than Ta1 is applied to the sensitive zone. The signal Ds1 measured by the detection means is stationary and is equal to the value of signal Sa1 at the end of step Ad1, which signifies that no event detectable by the detection means has taken place at Td1, notably no desorption. The species A, B and C desorb from the sensitive zone at a higher temperature at Td2.

During phase Ds2, a temperature Td2 greater than Td1 is applied. The signal Ds2 is in the order of 45%. The species A and B are desorbed.

During phase Ds3, a temperature Td3 greater than Td2 is applied. The signal Ds3 is in the order of 25%. Species C is desorbed. The signal Ds3 is not at 0% which signifies that other species different from the species of interest have been adsorbed.

During a cleaning phase CL1, the temperature TC1 greater than Td3 is applied to provoke desorption of remaining species, the signal Sc1 is at 0%. The sensor is ready for a new measurement.

During the first cycle, species C was able to be isolated, the difference between the signals Ds2 and Ds3 permit the determining of species C and the quantity of species C.

Now a second cycle of measurement is carried out to isolate A and B.

During a second measurement cycle, the heating means are commanded by the control means so as to apply during phase Ad2 a temperature Ta2 different from Ta1 in order to adsorb the species A and B but not the species C. The signal Sa2 is largely composed of a linear function characterising the adsorption on the sensitive zone, the maximum of Sa2 is in the order of 55%, less than 100% since at least species C is not adsorbed as well as other species without interest for the present measurement.

During phase Ds4 a temperature Td4 greater than Ta2 is applied to the sensitive zone. The signal Ds4 measured by the detection means is in the order of 30% it is stationary and less than signal Sa2, species A is desorbed.

During phase Ds5, a temperature Td5 greater than Td4 is applied. The signal Ds5 is in the order of 10%. Species B is desorbed. 10% of species of no interest have been adsorbed.

A cleaning phase CL2 takes place at a temperature TC2 greater than Td5, the signal Sc2 is at 0%, in the example shown TC1=TC2. The sensor is ready for a new measurement.

During this second cycle, the species A and B have been separated and the specific signals for these two species have been obtained permitting the determining of the quantity of each of the species.

It shall be understood that the number of cycles may vary depending on the number of species of interest to detect. The adsorption and desorption temperatures are selected in relation to the species that we wish to detect.

In the case of a dynamic functioning mode, the temperature profile and the signal from the detection means as a function of time t obtained shall be similar to those in FIG. 10, but we vary the frequency and/or amplitude of the activation function.

Figure 3:
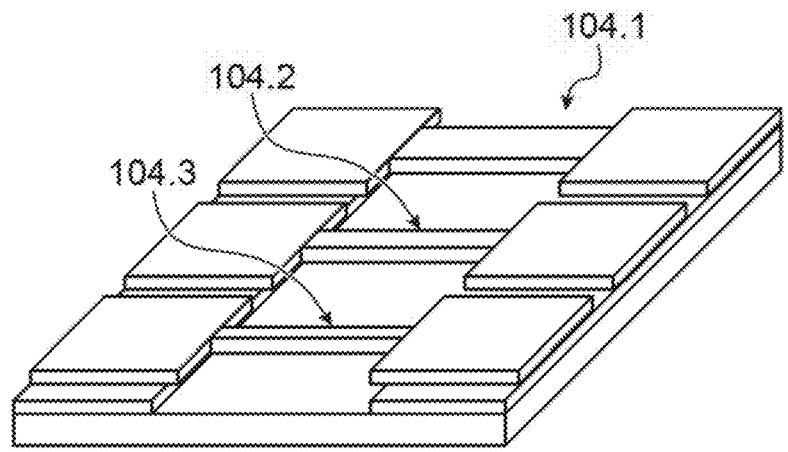
FIG. 3 is a perspective representation of one embodiment of one sensitive zone able to be implemented in a sensor according to the invention.

In FIG. 3, we see another example of an embodiment of a sensor according to the invention comprising several suspended parts 104.1, 104.2, 104.3 formed by suspended beams and arranged in parallel to each other. The beams all have different cross-sections, so that surface of the sensitive zone varies from one beam to another. In another variant, the beams cross each other.

For example, it can be foreseen to heat each sensitive zone to a different temperature to carry out measurements simultaneously at different temperatures, for example thus permitting to adsorb or desorb certain species on one sensitive zone and other species on other sensitive zones.

The sensor in FIG. 3 may be arranged in a channel. All the sensitive zones are heated to the same temperature, each sensitive zone adsorbs in the same proportion the same species, however, the quantity of species adsorbed is greater in the sensitive zones with a greater surface. By comparison we can distinguish the relative measurement of the species adsorbed and desorbed and correct the different shortcomings, such as drift. By comparing the signal from 104.1 and 104.3 and by observing the difference between the two signals we can suppress the signal variations (noise, drift) that are linked to unwanted effects of adsorption/desorption (temperature, pressure) and thus observe the component of the signal which is linked to the adsorption/desorption of gaseous species on the part of the sensitive layer of 104.1 which is in excess in relation to the sensitive layer of 104.3. The response supplied by sensitive layer 104.1 should be stronger than that supplied by sensitive layer 104.3, but should also be more affected by the artefacts. By combining the two responses, we can reduce the interference of other gases on the installation.

Figure 4:
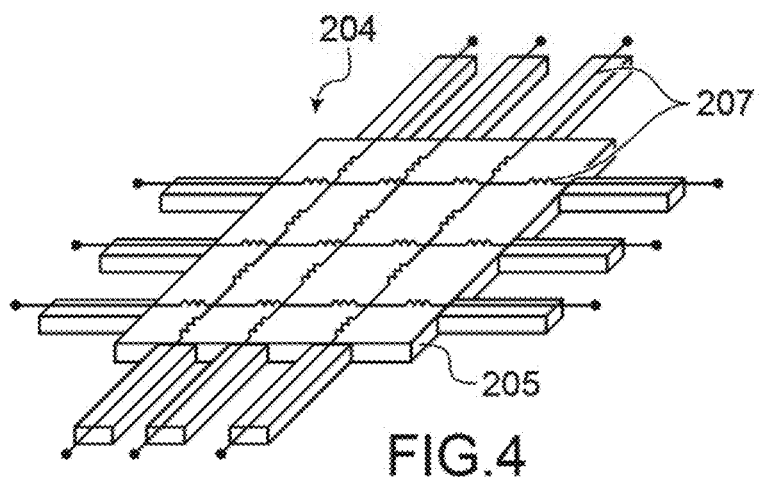
FIG. 4 is a perspective representation of a sensitive zone able to be implemented in a sensor according to the invention.

In FIG. 4, is shown another example of the sensor in which suspended part 204 comprises a membrane 205 on which is a network of electrical conductors 207 covering the membrane. In the example shown the electrical conductors 207 form a grid. By supposing that the sensitive zone covers the entire membrane, we can for example measure the resistance of a conductor or several coupled conductors which permits detection of the phases of adsorption and desorption at different locations of the sensitive zone. We can then work at different temperatures simultaneously and for example deduce information from the measurement noise and consequently correct the measurements.

Very advantageously, the control means are programmed so as to, in the case where the variation of the physical property measured for detection is less than a threshold value during the adsorption phase, we consider that the desorption step or steps have not taken place since the environment does not contain any or sufficient of the single or plural species of interest. This mode of operation permits reducing the energy consumption of the sensor. In the case where the sensor is used to detect the presence of pollutants or dangerous substances, this detection during the adsorption below the threshold value can permit us to conclude that the environment is deprived of these species and is thus safe. Very advantageously, a cleaning step takes place to replace the sensitive zone in a reference state.

As has already been mentioned, the control means can be of the adaptive type and thus modify the control signals of the heating means in relation to the output signals delivered by the detection means. For example, the temperature profile first applied comprises an isotherm adsorption and an isotherm desorption and the following profiles can, for example, comprise an isotherm adsorption and desorptions at different isotherms or with increasing temperature in order to better target the species and separates them. This adaptability can be particularly interesting when we do not know the number of species of interest contained in the environment or gaseous mixture.

The control means can furthermore be programmed to carry out a cleaning step of the sensitive zone by applying a temperature sufficiently high so as to desorb all the species of interest or otherwise. The efficiency of the cleaning is verified by analysing the signals from the detection means which must correspond to a sensitive zone free of all species or at least correspond to a sensitive zone in a known state of reference.

In one advantageous embodiment, the measurement of the noise and the analysis of the temperature dependence of the spectrum of electrical noise to selected working conditions may be used to detect and discriminate between the gaseous species.

As indicated above, the sensor can be arranged in a channel or microchannel. The channel may have a variable cross-section, for example a cross-section that reduces in the direction of the flow, thus favouring the separation of the species.

For example, in the case of the sensor in FIG. 3 or more generally a sensor with a beam suspended by its extremities or offset, the beam(s) are preferably arranged orthogonally in the direction of the gas flow.

In one advantageous embodiment, additional heating means, for example electrical resistances, can be integrated into the microchannel so as to generate a thermal gradient in the channel and around the sensor and/or to control the properties of the environment of the sensor.

In another embodiment, the sensor can be associated with a pump, more particularly a micro pump. The micro pump, by generating a flow in the channel can permit cleaning of the sensitive zone(s) for example after a cleaning phase and desorption of all the adsorbed species. The pump also serves to establish a flow of gas controlled in the neighbourhood of the sensors which permits moving of one desorbed species from one sensitive zone to another sensor, to be adsorbed on another sensitive zone.

The pump or micro pump can be of the Knudsen type which is a bidirectional pump thermally activated. This pump has the advantage of having no moving parts. Such a pump in porous material with pores of 100 nm can generate a flowrate of 0.74 sccm. Such a pump is described for example in «*Knudsen pump driven by a thermoelectric material*», Kunal Pharas and Shamus McNamara, Published 29 Nov. 2010 • 2010 IOP Publishing Ltd—*Journal of Micromechanics and Microengineering*, Volume 20, Number 12

As described above, sensors can be produced with several suspended parts whose temperature is controlled by the same control means and one can produce detection systems implementing several sensors according to the invention, each sensor having its own control means.

For example, in a channel several sensors can be integrated in a manner similar to that shown in FIG. 3.

The sensors can have different characteristics, for example in terms of size, sensitive layer . . . . They can thus be distinguished from each other. Furthermore, they can incorporate different heating means from each other. Moreover, the control of the heating means can differ from one sensor to another, thus applying different temperature profiles. We can for example envisage that certain sensors adsorb certain species and that other sensors adsorb other species.

Figure 5:
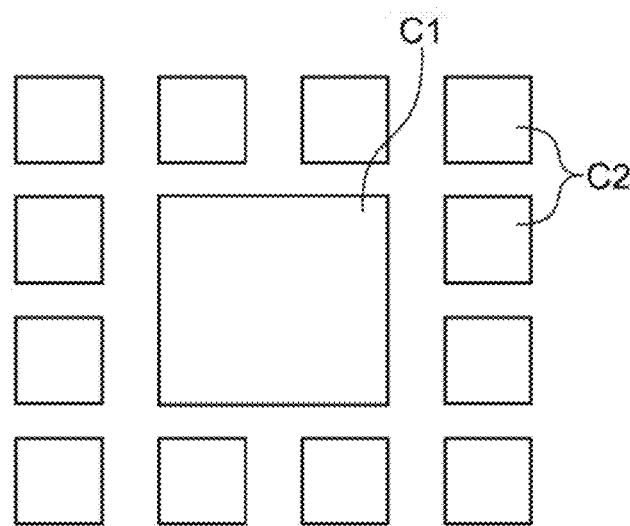
FIG. 5 is a schematic representation of a top view of a detection system for several sensors according to one embodiment.

In FIG. 5, is shown an example of an arrangement with a first sensor C1 according to the invention having a sensitive zone able to adsorb and desorb species and a plurality of second sensors C2 according to the invention arranged around the first sensor C1, and comprising a sensitive zone able to adsorb the species desorbed by the first sensor. The second sensors C2 allow analysis of the species desorbed by the first sensor. This combination is particularly interesting because the sensor according to the invention comprises heating means controlled according to given profiles and can separate the species or families of species adsorbed and the second sensors C2 analyse the separated species. In this example, the first sensor serves to separate and detect species or families of species. In a variant, the second sensors C2 could be gas sensors of prior art.

The information supplied by sensors C1 and C2 are complementary and are used in a complementary manner to deduce information about the gaseous species to be detected.

Figure 6:
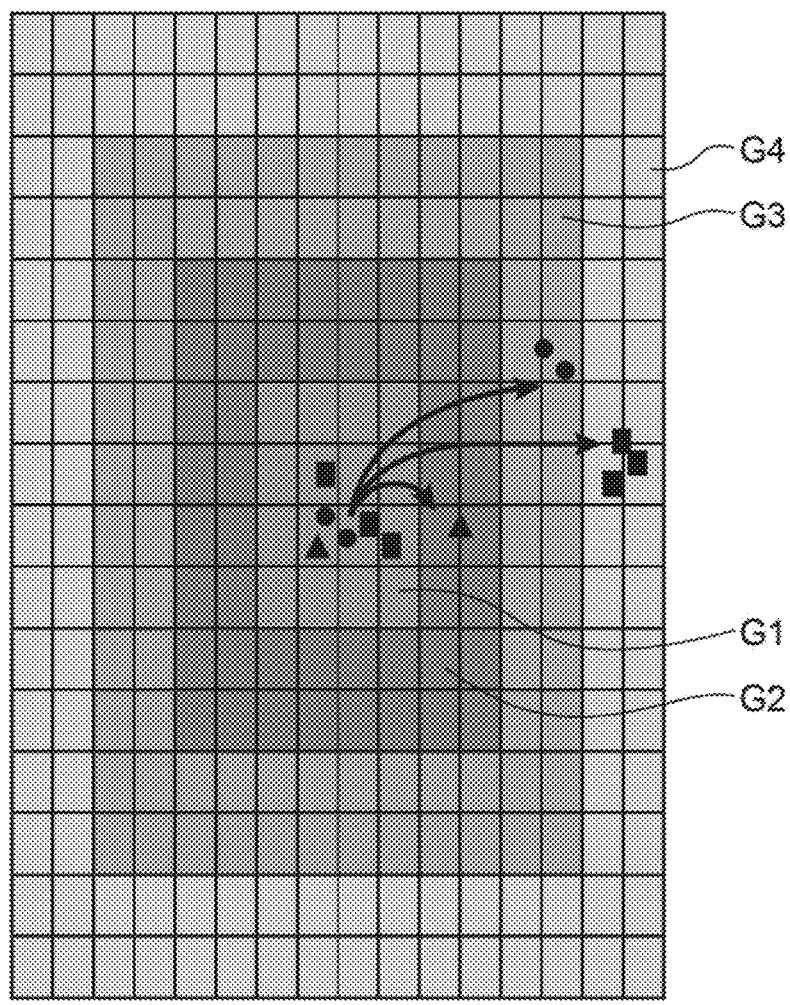
FIG. 6 is a schematic representation of the top view of a detection system for several sensors according to another embodiment.

In FIG. 6, we can see another example of an arrangement comprising a plurality of sensors according to the invention arranged in groups, for in the example shown, arranged in a concentric manner. Group G1 forms a block of sensors at the centre of the system, group G2 surrounds group G1, which itself is surrounded by group G3, itself surrounded by group G4.

Each group is at a given temperature so as to establish a temperature gradient between group G1 and group G4.

Group G1 adsorbs all the species then desorbs them, these species are then selectively adsorbed by one of the sensors of one of the groups in relation to its adsorption temperature. The temperature gradient also has the effect of provoking movement of the desorbed species. The sensitive zones can also be different, certain species adsorb on the active zones of one group and not on other groups. The different species are represented by the square, triangle and circle symbols.

The temperature of the sensors of group G1 can be controlled so as to ensure separation of the species or families of species.

Very advantageously the instants of adsorption of species are recorded by the sensors of each group, this permits to obtain information on the properties of stationary and dynamic adsorption and desorption and also to learn the speed of the movement of the species.

Furthermore, the imposed thermal gradient permits control of the direction of flow of the gas.

The amplitude, frequency and phase modulation of the temperature signals can be used to study their effects on the combined process of adsorption/desorption. In fact, the desorption/adsorption process is dependent on time, amplitude, frequency and modulation and is used to discriminate between the different gaseous species and to increase the selectivity of the sensor. For example, different zones can be activated by a particular activation signal, for example to produce a network of several sensors targeting different gaseous species with a view to producing a multipurpose sensor for several species.

We can envisage having several sensors arranged side by side but with sensitive layers that are highly different.

We can also foresee producing MEMS and/or NEMS systems comprising several sensitive zones, each on a distinct suspended part or on a single suspended part, with the sensitive zones being stacked.

The control means may also be programmed to apply thermal cleaning to all the sensors of all the groups, i.e. desorption of all the species in order to reset the sensors to a reference state.

Figure 7:
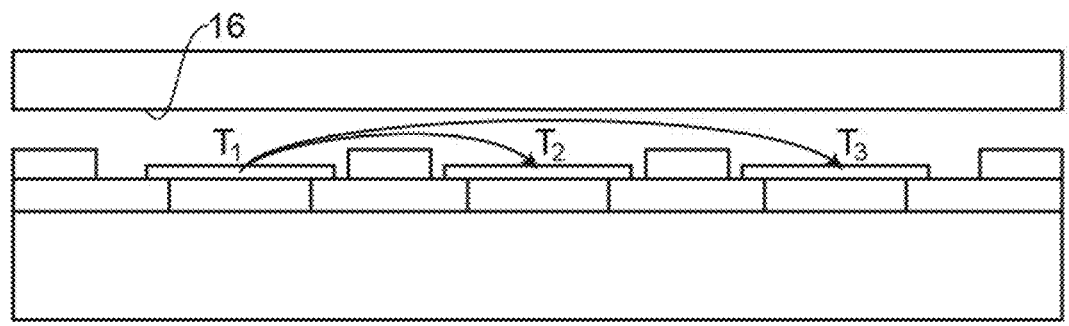
FIG. 7 is a longitudinal cross-section of one embodiment of a measurement system having several sensors according to the invention mounted in a fluidic channel.

In FIG. 7, is shown a detection system comprising a channel 16 in which several sensors are arrayed C1, C2, C3 alongside each other and along the axis of the channel, the sensitive zones not being in contact with each other. By applying a temperature gradient in the channel for example by heating means integrated in the channel or by heating means for each of the sensors, we can establish a gas flow in the channel, the gas entering into contact with each sensor successively.

Figure 8:
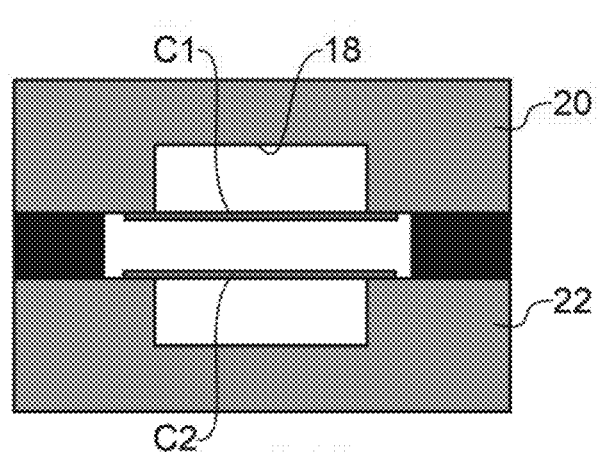
FIG. 8 is a transversal cross-section of another embodiment of a detection system for several sensors according to the invention in a fluidic channel.
Figure 9:
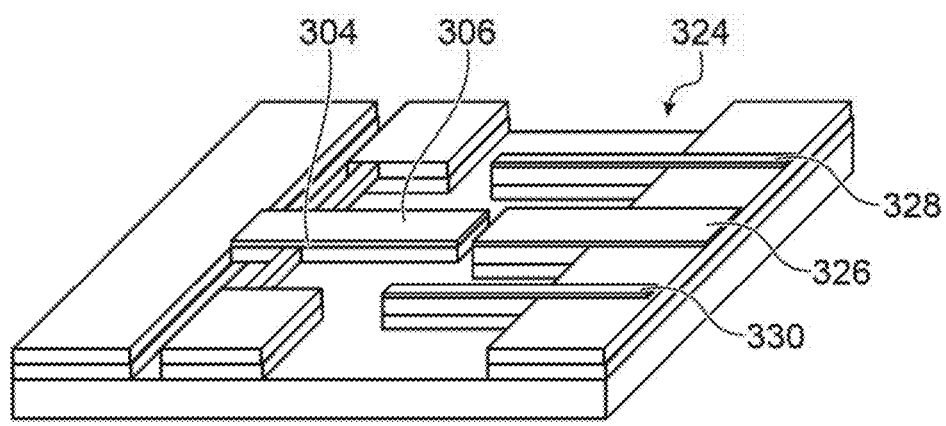
FIG. 9 is a perspective view of a detection system comprising a sensor according to the invention and a sensor of another type.

In FIG. 8, is shown two sensors arranged in a channel 18 largely in the same orthogonal plane as the axis of the channel. The channel is bordered by two substrates 20, 22 attached to each other in a tight manner. One sensitive zone of a sensor is suspended from a substrate and the sensitive zone of the other sensor is likewise suspended from the other substrate.

The sensors can each be arranged in relation to each other to improve the detection performance, for example in terms of selectivity and sensitivity, and/or to correct measurement errors, such as drift.

According to one embodiment, the sensors according to the invention may be arranged and connected in such a way as to permit differential measurements. For example, a first sensor is arranged in a gaseous environment to analyse and the second sensor is arranged in a controlled environment or is such that it is not sensitive to the same gases as the first sensor. The measurements can then be subtracted and permit removing drift due to variations in the measurement conditions.

According to another example, the sensors can be arranged and connected so as to permit comparative measurement. For example, we use several sensors having the same sensitive zones. For example we use three sensors aligned in a fluidic channel, the upstream sensor carries out an initial measurement of the gaseous mixture, the central sensor adsorbs the gaseous species of interest and the downstream sensor, which is identical to the upstream sensor, carries out a measurement on the gaseous mixture. The signals of the downstream sensor are compared to the signals of the upstream sensor and we can detect a difference or otherwise in the gaseous mixture resulting from adsorption by the upstream sensor.

A detection system according to the invention can also associate one of the sensors according to the invention and one or more sensors of one or more other types, the signal supplied by the sensors of different types permit improving the detection performance of the system.

The system comprises a sensor according to the invention having a suspended part 304 covered with a sensitive layer 306 intended to be placed in vibration, and an electrostatic actuator 324 intended to apply an electrical field to the suspended part 324 to place it in vibration. The actuator comprises three electrodes, one 326 in the centre and two 328, 330 on either side of the central electrode 326. The application of a difference in potential between the central electrode 326 and one of the other electrodes 328, 330 generates an electrical field which vibrates the suspended part 304. The suspended part 304 is arranged so as to undergo the electrical field. In the example shown, the suspended part 304 is aligned with the central electrode 326. Implementing all three electrodes allows the application of a non-uniform electric field to the suspended part. When the sensitive zone arranged on the suspended part adsorbs or desorbs species, the output signal frequency varies, the amplitude and deviation of the average value in relation to zero from the output signal being fixed by the electrodes of the actuator.

An example of the manufacturing process of a sensor according to the invention will now be described using FIGS. 11A to 11H.

During a first step, we use for example a substrate 1000 with on its front face a layer of silicon 1002 deposited on a sacrificial for example a layer of silicon oxide or silicon nitride 1004 and on the rear face a layer of silicon 1006 deposited on a layer of silicon oxide or silicon nitride 1008. In a variant a SOI (Silicon on Insulator) substrate could be used.

The layer of silicon 1002 is structured to form the MEMS and/or NEMS elements, such as the suspended part, the actuating means for example the electrodes in the case of a resonating sensor . . . layer 1002 is for example structured by depositing a resin and etching by means of hydrofluoric acid, or KOH or Rear Ionic Etching.

Figure 11A:
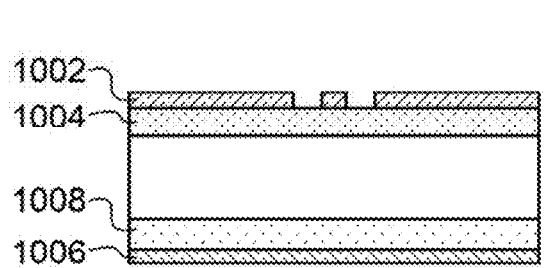
FIGS. 11A to 11H are schematic representations of the different steps of one embodiment of a manufacturing process for a sensor according to the invention.

The element thus obtained is shown in FIG. 11A.

In a following step, we produce the heating means on the suspended part, to do this an electrical conductor layer 1010, for example is metal formed on the structured layer 1002, this metal layer 1010 is intended to form the heating means. Previously a resin layer 1012 is formed on layer 1002 and is etched to access only the front face of the suspended part, or part of it. It can be also be foreseen to form a protective layer to separate the heating means from the sensitive layer.

Figure 11B:
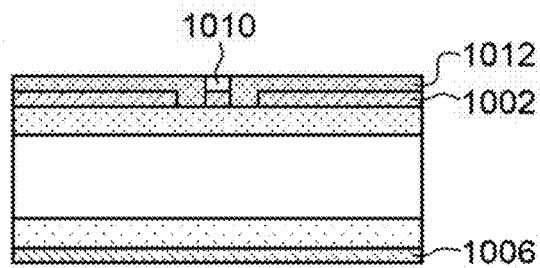

The element thus obtained is shown in FIG. 11B.

During a following step, a resin layer 1012' is deposited and etched to access layer 1002 in order to limit the metal deposition zones with a view to producing the interconnection contacts. Then, the interconnection contacts are produced by forming a metal layer 1013 on the resin layer 1012' and the etched zones.

We also etch silicon layer 1006 on the rear side.

Figure 11C:
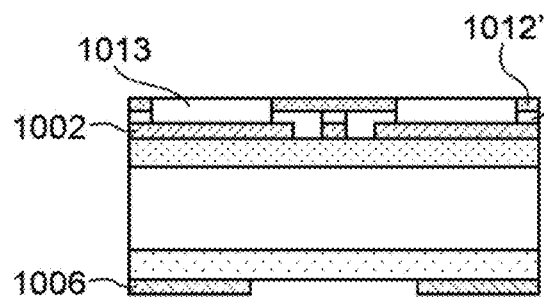

The element thus obtained is shown in FIG. 11C.

During a following step, layer 1012 is removed.

Figure 11D:
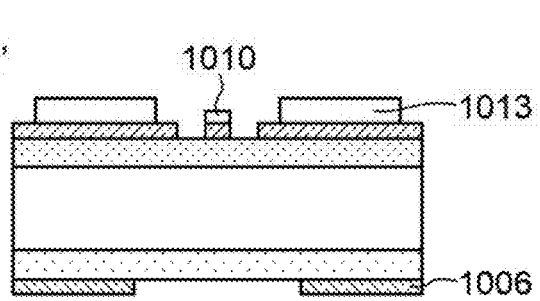

The element thus obtained is shown in FIG. 11D.

During the following step, the suspended part is freed for example by wet etching with HF or BOE or by a dry etch. The oxides and metals employed are chosen to resist this etching. The liberation is carried out by etching the rear face through the whole stack starting from the oxide layer 1008.

Figure 11E:
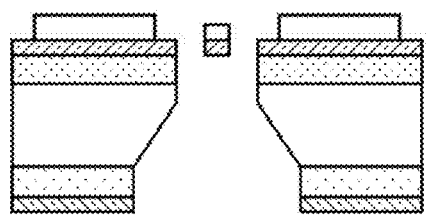

The element thus obtained is shown in FIG. 11E.

During a following step, we form the sensitive zone for example by depositing a sensitive layer 1014 directly on all or part of the suspended part.

The sensitive layer is for example produced by depositing chemical species in solution, for example using the Langmuir-Blodgett technique, by spin coating or by spraying.

In one variant, it can be formed by a gaseous phase deposition procedure, for example by chemical deposition in a vapour phase, depositing in vapour phase, or deposition in molecular vapor phase.

The deposition technique of the sensitive zone is such that it is formed by a thin film of a controlled and homogenous thickness, for example in the order of several tens to several hundreds of nm.

Figure 11F:
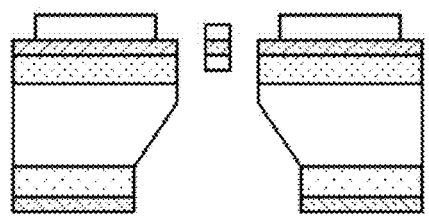

The element thus obtained is shown in FIG. 11F. In this example the sensitive layer is formed on one of the faces of the suspended part, but it could be formed on both sides of the suspended part.

In one variant, we produce an additional oxide layer 1016 on the MEMS and/or NEMS structure to form a planarization layer, for example in the case of fitting in a fluidic channel. Furthermore this can serve to protect the sensor from mechanical damage and the solutions employed in the remainder of the procedure.

The suspended part is freed for example by wet etch using HF or BOE or by a dry etch. The oxides and metals used are selected to resist this etch. In this variant, the liberation is obtained by etching only oxide layer 1004.

Figure 11G:
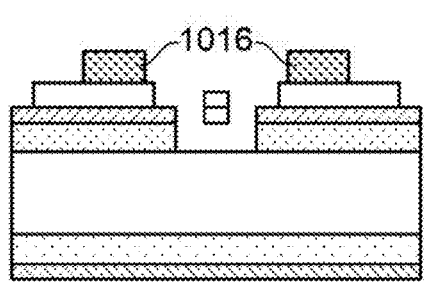

The element thus obtained is shown in FIG. 11G.

During a following step, the sensitive zone 1014' is formed on the suspended part as described above. In this variant, the sensitive zone 1014' is formed on the metal forming the heating means.

Figure 11H:
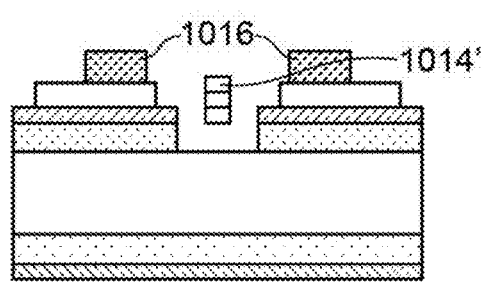

The element thus obtained is shown in FIG. 11H.

The sensitive zone can be formed before or after liberation of the suspended part.

Preferably when production of the sensitive zone requires a depositing of resin, the suspended part is liberated after production of the sensitive zone in order to avoid rupturing the suspension beams.

In the case where the sensitive zone is sprayed, it can be produced after liberation of the suspended part.

In the case where one wishes to integrate the sensor in a fluidic channel, we produce a second substrate in which the channel is etched. The two substrates are then assembled in a gas tight manner by using layer 1016 as the interface area. The gas tight assembly is carried out using an adhesive that does not interact with the gaseous species or more generally an adhesive that permits assembly of the substrates but which is not a contaminant in relation to the milieu to analyse, for example an Ordyl® type adhesive.

The sensor according to the present invention can be used in a very high number of applications. For example, it can be used as a humidity sensor, a chemical or biological sensor.

It can be used for mass spectroscopy, or thermal desorption spectroscopy.

This sensor can be used to verify the quality of indoor air.

The sensor being reliable in operation, requires little maintenance and consumes little energy, it can be integrated into portable electronic devices such as mobile phones or tablet computers.

The sensor can also be easily integrated into or after a gas phase chromatography micro column.

The invention claimed is:

1. A gas sensor configured for analysis of a mixture of at least two gaseous species or at least two families of gaseous species to be detected, said gas sensor comprising:
   a fixed part,
   at least one suspended part in relation to the fixed part,
   at least one sensitive zone carried on the at least one suspended part, said at least one sensitive zone being configured to adsorb/absorb and desorb gaseous species or families of gaseous species,
   a heater configured to heat the at least one sensitive zone,

17 a detector configured to detect the adsorption/absorption and the desorption of the gaseous species or the families of gaseous species, on the at least one sensitive zone, a controller configured to
control the heater to heat the at least one sensitive zone to at least one first temperature to cause the adsorption/absorption of at least one of the gaseous species or the families of gaseous species,
control the detector to generate an adsorption/absorption detection signal in response to the adsorption/absorption,
control the heater to heat the at least one sensitive zone to at least one second temperature to cause the desorption of a part of the gaseous species or the families of the gaseous species,
control the detector to generate a desorption detection signal in response to the desorption, and
repeat a cycle of the steps of heating the at least one sensitive zone to at least one first temperature and heating the at least one sensitive zone to at least one second temperature, wherein the at least one first temperature applied during a repetition of the cycle is greater than a previous at least one first temperature applied during a previous cycle, the at least one second temperature applied during a repetition of the cycle is greater than a previous at least one second temperature applied during a previous cycle, the repetition of the cycle is performed until all gaseous species of interest or families of gaseous species of interest are desorbed, and the at least one sensitive zone of the at least one suspended part is in the mixture of the at least two gaseous species or the at least two families of gaseous species to be detected.

2. The gas sensor according to claim 1, further comprising a temperature sensor for measuring a temperature of the at least one sensitive zone.

3. The gas sensor according to claim 1, wherein the at least one suspended part is mobile and the detector comprises an actuator configured to move the at least one suspended part and a movement sensor configured to measure the movement of the at least one suspended part.

4. The gas sensor according to claim 1, wherein the at least one suspended part is at least in part an electrical conductor and the detector measures a variation in conductivity of the at least one suspended part.

5. The gas sensor according to claim 4, wherein the heater and the detector are integrated into the at least one suspended part.

6. The gas sensor according to claim 1, wherein the heater is a Joule effect heater.

7. The gas sensor according to claim 6, wherein the at least one suspended part is at least partially an electrical conductor and heats by Joule effect via circulation of a current.

8. The gas sensor according to claim 1, further comprising a database of temperature profiles.

9. The gas sensor according to claim 1, wherein the at least one suspended part includes several suspended parts with respective sensitive zones of different surface areas and/or having properties of adsorption/absorption and desorption different from each other.

10. The gas sensor according to claim 1, wherein the controller is configured to control the heater to respectively heat different zones of the at least one suspended part to different temperatures simultaneously.

11. An analysis method for analysis of a gaseous mixture of at least two gaseous species or at least two families of gaseous species implementing a sensor according to claim 1, comprising:
a) heating at least one sensitive zone in a reference state to the at least one first temperature to provoke an adsorption/absorption of gaseous species or families of gaseous species,
b) measurement of the adsorption/absorption detection signal,
c) application of the at least one second temperature to provoke the desorption of the part of the gaseous species or families of gaseous species,
d) measurement of the desorption detection signal,
e) repetition of steps a), b), c) and d) until all the gaseous species of interest or families of gaseous species of interest are separated, wherein the at least one first temperature and the at least one second temperature applied at each cycle of repetition are respectively greater than the at least one first temperature and the at least one second temperature of a previous cycle of repetition, and the at least one sensitive zone of the at least one suspended part is in the mixture of the at least two gaseous species or the at least two families of gaseous species to be detected.

12. The analysis method according to claim 11, further comprising determining adsorption/absorption and desorption conditions of a next repetition in relation to the measured desorption detection signal of a current repetition.

13. The analysis method according to claim 11, further comprising determining the at least one second temperature of step c) in relation to the measured adsorption/absorption detection signal obtained in step b).

14. The analysis method according to claim 11, further comprising, at least prior to step a), at least one cleaning step carried out by application of a temperature provoking a desorption such that the at least one sensitive zone returns to its reference state.

15. The analysis method according to claim 11, further comprising interrupting the analysis method when a value of the adsorption/absorption detection signal of step b) is less than a threshold value.

16. A gas detection system comprising at least one first gas sensor according to claim 1, at least one second gas sensor including a detector and at least one sensitive zone, and a comparator and signal processing device issuing from the detector of each of said gas sensors.

17. The gas detection system according to claim 16, wherein the at least one second gas sensor is located in a reference environment.

18. The gas detection system according to claim 16, wherein the at least one second gas sensor is a gas sensor according to claim 1, wherein the at least one first gas sensor and the at least one second gas sensor are located in the gaseous mixture, at least one sensitive zone of the at least one first gas sensor and at least one sensitive zone of the at least one second gas sensor being configured to adsorb/absorb and desorb different gaseous species or families of gaseous species.

19. The gas detection system according to claim 18, wherein the at least one first gas sensor includes several first gas sensors and the at least one second gas sensor includes several second gas sensors sharing a common controller, wherein the several second gas sensors are spread in several groups arranged in a concentric manner around the several first gas sensors, the controller of the several second gas sensors controlling heaters of the several second gas sensors such that sensitive zones of each group are at a different temperature from sensitive zones of other groups.

20. The gas detection system according to claim 16, wherein the at least one second gas sensor includes several second gas sensors sharing a common controller, the several second gas sensors being arranged around the at least one first gas sensor, the controller of the several second gas sensors controlling heating of the respective sensitive zones of the several second gas sensors such that the several second gas sensors adsorb/absorb the gaseous species or families of gaseous species desorbed by the at least one first gas sensor.

21. The gas detection system according to claim 16, wherein
- the at least one second gas sensor comprises plural second gas sensors, at least one of the plural second gas sensors is arranged upstream of the at least one first gas sensor,
- at least one of the plural second gas sensors is arranged downstream of the at least one first gas sensor, and
- the gas detection system further comprising a comparator for comparing signals supplied by the detectors of the plural second gas sensors.

22. The gas detection system according to claim 16, further comprising a channel wherein the at least one first gas sensor and the at least one second gas sensor are mounted.

23. The gas detection system according to claim 22, further comprising a pump connected to the channel.

* * * * *